(12) United States Patent
Bardonnet et al.

(10) Patent No.: US 7,709,462 B2
(45) Date of Patent: May 4, 2010

(54) IMPLANTABLE AND BIOCOMPATIBLE GELLABLE COMPOSITION

(75) Inventors: Raphael Bardonnet, Vert-Saint-Denis (FR); Laurent Laganier, Vernaison (FR)

(73) Assignee: TB-Genie Tissulaire, Mions (FR)

( * ) Notice: Subject to any disclaimer, the term of this patent is extended or adjusted under 35 U.S.C. 154(b) by 0 days.

(21) Appl. No.: 10/466,819

(22) PCT Filed: Jan. 22, 2002

(86) PCT No.: PCT/FR02/00262

§ 371 (c)(1),
(2), (4) Date: Sep. 23, 2003

(87) PCT Pub. No.: WO02/057355

PCT Pub. Date: Jul. 25, 2002

(65) Prior Publication Data

US 2004/0047912 A1     Mar. 11, 2004

(30) Foreign Application Priority Data

Jan. 22, 2001    (FR) .................................. 01 00832

(51) Int. Cl.
*A61K 9/14* (2006.01)
*A61K 45/00* (2006.01)

(52) U.S. Cl. ........................... 514/54; 514/57; 530/614; 424/93.7; 424/94.6; 424/488

(58) Field of Classification Search ................ 424/93.7, 424/94.6, 427; 514/54, 57; 530/813, 814
See application file for complete search history.

(56) References Cited

U.S. PATENT DOCUMENTS 4,478,822 A * 10/1984 Haslam et al. ............. 424/94.6
4,676,976 A *  6/1987 Toba et al. .................. 424/485
5,587,175 A * 12/1996 Viegas et al. ............... 424/427
6,060,053 A *  5/2000 Atala ........................ 424/93.7
6,129,761 A * 10/2000 Hubbell ................... 623/23.72

FOREIGN PATENT DOCUMENTS

| JP | 62296853 | 12/1987 |
| JP | 62296853 A2 * | 12/1987 |
| WO | WO 91/01720 | 2/1991 |
| WO | WO 98/40111 | 9/1998 |
| WO | WO 99/15211 | 4/1999 |

OTHER PUBLICATIONS

Alberts et al. Molecular Biology of the Cell, Third Edition. Garland Publishing., 1994. pp. 1179-1186.*
Budavari et al. The Merck Index, Twelfth Edition. CRC Press., 1996. Monograph 182.*
Vacanti et al. Lancet 1999; 354 (supp. 1) pp. 32-34.*
Vacanti , Lancet, 1999, 354 (supp 1) 32-34.*
Alberts, (Molecular Biology of the Cell, 3rd edition, 1994.*
Budavari , The Merck Index, 12th edition, 1996.*
Goodman et al, The Pharmacological Basis of Therapeutics, 10th ed., 1996, pp. 54-57.*
Pedraz et al , Biotech. Bioengg. 2001, 76(4), 285-294.*
Alberts (Molecular Biology of the Cell, 3rd edition, 1994.*
Goodman and Gilman's "The Pharmacological Basis of Therapeutics", 10th Ed., 1996, p. 54-57.*
Dumitriu, S. Polysaccharides in Medicinal Applications, Marcel Dekker, 1996, pp. 140-141 and 203-207.*
XP-002178518; Tenihiko Sato; Hokusuishi Geppo, vol. 24, No. 9, 1967 pp. 350-356 w/abstract.

* cited by examiner

*Primary Examiner*—Shaojia Anna Jiang
*Assistant Examiner*—Ganapathy Krishnan
(74) *Attorney, Agent, or Firm*—Oliff & Berridge, PLC

(57) ABSTRACT

The invention concerns an aqueous biocompatible gel composition of polysaccharides characterized in that it comprises a mixture of at least two polysaccharides one of which is capable of being gelled by chemical process and the other by heat process and the use of such a composition for preparing an implant. The inventive composition is characterized in that it further contains biological tissue extracts and/or an active pharmaceutical principle alone or combined.

12 Claims, No Drawings

IMPLANTABLE AND BIOCOMPATIBLE GELLABLE COMPOSITION

The present invention relates to the formulation and the shaping of biocompatible gellable compositions for producing implants.

In the field of the healing of tissues such as cartilage or bone tissues, it is often necessary to resort to chondrocyte transplants.

These chondrocyte transplants use, to date, cell suspensions which are sometimes difficult to use and, as a result, there is a need for a product or for means for carrying out these chondrocyte transplants using solid materials exhibiting mechanical characteristics which allow easy handling.

Biodegradable materials are known, namely, for example, natural polymers such as celluloses, methylcelluloses, gelatins, caseins, chitosans, polylysines or polysaccharides.

The properties, for example gelling properties, of some of these biomaterials, such as polysaccharides, which make it possible to produce solid products, and their biocompatibility which is sufficient to maintain cell viability, are also known. It is thus known practice to keep cells alive in media containing natural polysaccharides, and the inclusion of living material or of pharmaceutical active principles in gels consisting of polysaccharides is therefore possible.

Macromolecular natural polysaccharides are composed of nonhydrolyzed saccharide molecules linked to one another so as to form long chains.

The macromolecules can be composed of approximately 3 000 saccharide molecules, and preferably of 300 to 1 200 molecules.

Various means and methods have been used to obtain alginate gels which can be used as an implantable material which may or may not contain living tissue extracts and/or pharmaceutical active principles.

An alginate gel composed of a suspension of hydrogel particles having a diameter of between 30 and 500 µm is, for example, known from WO 98/25053.

A composite material is known, from GB 2201966, which consists of two gellable compounds, in which part of one of the two gellable compounds is removed, thus making it possible to form a porous composite gel having cavities containing, for example, cells.

The influence of solutions of metal cation salts on the hardness of gels consisting of agar and of sodium alginate is known from the publication Hokusuishi Geppo (1967), 24, 350-6.

More recently, for applications in the food domain, the use of compounds whose gelling process is thermo-reversible in a mixture with sodium alginate has been revealed in JP62296853, to produce gels capable of withstanding high temperatures, while at the same time being relatively non-distortable.

Macromolecular natural polysaccharides are composed of nonhydrolyzed saccharide molecules linked to one another so as to form long chains.

The macromolecules can be composed of approximately 3 000 saccharide molecules, and preferably of 300 to 1 200 molecules.

Among the solutions previously implemented, none have to date made it possible to prepare implants exhibiting mechanical properties compatible with their use in surgical acts and easy handling.

It is, for example, known practice to use alginate gels. Alginates are derivatives of algin, which is a complex polysaccharide present in the cell walls of a brown algae belonging to the phaetophyceae group. The alginate is extracted from the algae in the form of a sodium salt solution.

Alginates exhibit in particular the property of forming gels by reaction with divalent cations. These gels generally consist of approximately 97.5 to 99% of water, and 0.3 to 2.5% of polymers.

The inclusion of living material or of pharmaceutical active principles is possible; in particular, it is known practice to use alginate gels to maintain cells in suspension. Said cells can, for example, be dispersed in a solution of alginate which will be polymerized upon contact with a solution of calcium or barium salt.

However, this method of polymerization does not make it possible to form a block of gel which can be shaped, nor does it enable molding. Independent beads of a gel which nevertheless exhibits advantageous mechanical characteristics, since it is not crumbly, it can be handled, and it can even be cut up, are obtained.

Among the other polysaccharides which can be used, there is known to be agarose, which is derived from the agar extracted from various sorts of red algae belonging to the rhodophyceae group; it is a linear hydrocolloid galactan.

Agar and agaroses have the property of forming gels by cooling; these gels exhibit physical properties which are variable depending on the origin of the agars or of the agaroses. These polysaccharides can therefore be readily shaped due to their gelling properties as a function of temperature, for example by molding under hot conditions. They can also, by working with a solution, be molded at a temperature above the gelling temperature, and then, after cooling, be removed from the molds.

These agars or agaroses also have the particularity of exhibiting gelling temperatures of less than 40° C., compatible with cell life and below the temperatures of degradation of many pharmaceutical active principles. However, the mechanical characteristics of these gels are insufficient since they are crumbly and brittle and do not withstand the constraints imposed during the performance of surgical acts.

The present invention makes it possible to produce implants exhibiting mechanical properties compatible with their use in particular during surgical acts and allowing chondrocyte transplantation.

The present invention also relates to a biocompatible and gellable aqueous composition of polysaccharides, characterized in that it comprises a mixture of at least two polysaccharides, one of which is chemically gellable and the other of which is thermally gellable.

A gellable polysaccharide is thus a polysaccharide exhibiting the property of forming a gel by crosslinking, such as alginates, agaroses or chitosans.

The crosslinking is carried out, depending on the nature of the polysaccharides used, by decreasing the temperature or by adding a saline solution, for example containing calcium or barium ions, or by modifying the pH.

The term "thermally gellable" is here intended to mean the ability of a composition to form a gel via a decrease in temperature.

The term "chemically gellable" is here intended to mean the ability of a composition to form a gel via reaction, for example, with metal cations which cause crosslinking and therefore gel formation, or by modification of the pH of the polysaccharide solution.

The chemically gellable polysaccharides according to the invention are chosen from alginates, chitosans and collagen.

Chitosans consist of N-acetylglucosamine residues linked by beta-1,4 linkages, derived by deacetylation of chitin which forms long chains. Chitin is the main constituent of the exoskeleton of crustacea.

Collagen is a complex scleroprotein which is insoluble in water and saline solutions, which is converted to gelatin in boiling water, and which is made up of tropocollagen macromolecules. Collagen is the essential component of the fibrils and fibers of the connective tissue.

The thermally gellable polysaccharides according to the invention are agar or agarose.

The two preferred polysaccharides according to the invention are agarose and alginate.

The aqueous compositions of polysaccharides according to the invention contain between 0.5 and 10% of chemically gellable polysaccharide and between 0.5 and 10% of thermally gellable polysaccharide.

The present invention relates to a biocompatible and gellable aqueous composition of polysaccharides, one of which is chemically gellable and the other of which is thermally gellable, this mixture making it possible, by formation of the gel by crosslinking via a decrease in temperature, to create a moldable and solid structure, then making it possible, by chemical crosslinking of the second polysaccharide, to improve the mechanical properties.

The present invention relates to a biocompatible and gellable aqueous composition of polysaccharides, one of which is chemically gellable and the other of which is thermally gellable, characterized in that it comprises living biological tissue extracts or autologous, allogenic or xenogenic cells.

The cells which can be used in a composition according to the invention belong to the group of chondrocytes and other cells constituting cartilage, to the group of osteoplasts or other cells constituting bone, to the group of muscle cells or fibroblasts.

These cells will preferably be chosen from cells capable of stimulating bone or cartilaginous tissue regeneration.

The cells capable of stimulating cartilaginous tissue regeneration are, for example, chondrocytes isolated and multiplied by cell culture from cartilage biopsy.

The biocompatible gellable compositions prepared according to the invention can also contain demineralized spongy bone.

The biocompatible gellable compositions prepared according to the invention can also contain agents capable of treating or preventing pathological conditions or complications.

These agents are, for example, pharmaceutical active principles such as, for example, antiviral agents or antibacterial agents.

These agents can be present in the biocompatible gellable compositions according to the invention alone or as mixtures.

The compositions according to the invention are prepared using the method comprising the following steps:
  solubilization of the chemically gellable polymer in water,
  addition of the thermally gellable polysaccharide and dissolving by heating,
  sterilization and cooling.

A partially crosslinked intermediate gel is produced, which is optionally redissolved by heating before addition of the cell suspensions or of the pharmaceutical active principles.

cooling of the mixture obtained for thermal gelling and molding, an intermediate form is therefore obtained which does not exhibit the mechanical properties required for the use;

removal from the mold and then gelling by chemical crosslinking, by bringing into contact with a saline solution.

This method also makes it possible to obtain, if necessary, sterilizable intermediate gels which are ready to use for the incorporation of active principles and/or of cell suspensions.

In a preparation variant, the chemical gelling can be carried out in situ at the time of implantation or after implantation by addition of a saline solution.

The saline solutions according to the invention are preferably solutions of calcium or barium salts.

EXAMPLES OF USE

I. Implant Containing Chondrocytes Intended for Joint Cartilage Repair

Production of an implant containing chondrocytes

The implant is made up of cultured chondrocytes, of a composite gel and, optionally, of human demineralized spongy bone.

Preparation of the Chondrocytes

The chondrocytes originate from a cartilage biopsy performed on a patient suffering from chondral or osteochondral lesions. After isolation using a suitable enzyme treatment, the chondrocytes are multiplied in cell culture until a sufficient number are obtained. All the steps for obtaining the chondrocytes are carried out in aseptic medium.

These cells are then recovered and suspended in culture medium before production of the implant.

Preparation of the Demineralized Spongy Bone:

The human bone tissue originates from a tissue bank. It undergoes a step of devitalization and of viral inactivation by chemical and physical action. The bone tissue is adjusted to the desired form and then demineralized in acid medium at 4° C. The sterile condition is obtained by gamma radiation.

Preparation of the Composite Gel:
1. Alginate is dissolved in a Hank's solution at ambient temperature at a concentration generally between 1 and 10%.
2. "Low gelling" agarose is suspended in the preceding mixture at a concentration generally between 1 and 10%.
3. After homogenization, the mixture is immediately heated to 90° C. in order to dissolve the agarose in suspension.
4. The solution of alginate and agarose is sterilized by autoclaving at 121° C. for 20 minutes.
5. The composite gel forms after cooling to agarose gelling temperature.

Preparation of the Implant

All of the operations are carried out under aseptic conditions
1. The composite gel is liquefied by heating at 90° C. and is then kept at 37° C. for use.
2. The cell suspension is added.
3. After homogenization, the mixture is poured into a mold.
4. For the implants with bony phase, the demineralized spongy bone is then added as needed.
5. The mold is then brought to 4° C. for 10 minutes to allow the implant to gel.
6. The implant is removed from the mold and is then immersed in a 25 mM $CaCl_2$ solution for 10 minutes in order to convert the sodium alginate to calcium alginate.
7. The implant is incubated at 37° C., 5% $CO_2$, in DMEM medium adjusted to give 3 mM $CaCl_2$, until use.

Preparation Variant

When the implant does not contain demineralized bone, it is possible to convert the sodium alginate to calcium alginate only in situ at the time of implantation. The implant is then used as a paste which is shaped in the lesion to be treated. Spraying a solution containing 20 mM of calcium chloride causes the implant to solidify in situ, adopting the shape of the lesion.

II. Femoral Obturator Intended to Facilitate Placing Pressure on Surgical Cement and to Limit its Progression Into the Diaphyseal Canal of the Femoral Shaft During Hip Replacement The obturators conventionally used are either made of biodegradable synthetic materials (polymer of lactic or glycolic acid), or based on gelatin of animal origin (generally porcine origin). In the first case, lysis of the polymer causes inflammatory phenomena which are undesirable. In the second case, the use of a product of animal origin represents a potential risk of transmission of infectious diseases (prions).

Production of a Femoral Obturator
1. Alginate is dissolved in water for injectable preparation, at a concentration generally between 1 and 10%.
2. "High gelling" agarose is suspended at a concentration generally between 1 and 10%.
3. The mixture is immediately brought to a temperature above the melting temperature of the agarose, in a mixer, while at the same time homogenizing.
4. The gel is poured into obturator molds preheated to 50° C.
5. The molds are allowed to cool for 30 minutes at 4° C. and the gel is then removed from the molds.
6. The obturators are immersed in a 100 mM $CaCl_2$ solution for 12 hours.
7. The obturators are rinsed for two times one hour in injectable quality physiological saline.

The invention claimed is:

1. A molded gel implant comprising a biocompatible and gellable aqueous composition of polysaccharides, the composition consisting of a mixture of two polysaccharides,
    wherein one of the two polysaccharides is chemically gellable and the other of the two polysaccharides is thermally gellable,
    wherein the chemically gellable polysaccharide is a calcium alginate,
    wherein the thermally gellable polysaccharide is selected from the group consisting of agarose and agar,
    wherein the biocompatible and gellable aqueous composition contains biological tissue extracts, which are autologous, allogenic or xenogenic cells selected from the group consisting of chondrocytes, cells constituting cartilage, osteoblasts, cells constituting bone, muscle cells and fibroblasts, and
    wherein the molded gel implant is obtained by thermal gelling followed by chemical gelling of the biocompatible and gellable aqueous composition.

2. A molded gel implant comprising a biocompatible and gellable aqueous composition of polysaccharides, the composition consisting of a mixture of two polysaccharides,
    wherein one of the two polysaccharides is chemically gellable and the other of the two polysaccharides is thermally gellable,
    wherein the chemically gellable polysaccharide is a calcium alginate,
    wherein the thermally gellable polysaccharide is selected from the group consisting of agarose and agar,
    wherein the biocompatible and gellable aqueous composition contains at least one pharmaceutically active principle chosen from the group consisting of antiviral agents and antibacterial agents, and
    wherein the molded gel implant is obtained by thermal gelling followed by chemical gelling of the biocompatible and gellable aqueous composition.

3. A molded gel implant comprising a biocompatible and gellable aqueous composition of polysaccharides, the composition consisting of a mixture of two polysaccharides,
    wherein one of the two polysaccharides is chemically gellable and the other of the two polysaccharides is thermally gellable,
    wherein the chemically gellable polysaccharide is a calcium alginate,
    wherein the thermally gellable polysaccharide is selected from the group consisting of agarose and agar,
    wherein the biocompatible and gellable aqueous composition contains demineralized spongy bone, and
    wherein the molded gel implant is obtained by thermal gelling followed by chemical gelling of the biocompatible and gellable aqueous composition.

4. The molded gel implant as claimed in claim 1, wherein the polysaccharides are respectively present in the gel at a concentration between 0.5 and 10%.

5. A method of preparing an implant, consisting essentially of:
    preparing a composite gel that comprises a biocompatible and gellable aqueous composition of polysaccharides consisting of a mixture of two polysaccharides, wherein one of the two polysaccharides is chemically gellable and the other of the two polysaccharides is thermally gellable, by:
    solubilization of the chemically gellable polysaccharide in water, wherein the chemically gellable polysaccharide is an alginate,
    addition of the thermally gellable polysaccharide and dissolving by heating, wherein the thermally gellable polysaccharide is selected from the group consisting of agarose and agar,
    homogenization of the mixture,
    casting the mixture into a mold,
    cooling of the mixture obtained for thermal gelling and molding, and
    removing the thermally gelled and molded composition from the mold and then gelling by chemical crosslinking by bringing the thermally gelled and molded composition into contact with a calcium saline solution.

6. A method for preparing a molded gel of polysaccharides, comprising:
    solubilization of a chemically gellable polysaccharide in water, wherein the chemically gellable polysaccharide is an alginate,
    addition of a thermally gellable polysaccharide to the chemically gellable polysaccharide and dissolving the thermally gellable polysaccharide by heating to form a mixture, wherein the thermally gellable polysaccharide is selected from the group consisting of agarose and agar,
    sterilization and cooling,
    production of a partially crosslinked intermediate gel,
    solubilization of the intermediate gel by heating,
    addition of the pharmaceutically active principles selected from the group consisting of antiviral agents and antibacterial agents and/or of the biological tissue extracts, which are autologous, allogenic or xenogenic cells selected from the group consisting of chondrocytes, cells constituting cartilage, osteoblasts, cells constituting bone, muscle cells and fibroblasts and/or of demineralized spongy bone,
    casting the mixture into a mold, cooling of the mixture obtained for thermal gelling and molding, removal from the mold and then gelling by chemical crosslinking, by bringing the thermally gelled and molded composition into contact with a calcium saline solution.

7. A method for preparing a femoral obturator, consisting essentially of:

solubilization of a chemically gellable polysaccharide in water, wherein the chemically gellable polysaccharide is an alginate, addition of a thermally gellable polysaccharide to the chemically gellable polysaccharide and dissolving the thermally gellable polysaccharide by heating to form a mixture, wherein the thermally gellable polysaccharide is selected from the group consisting of agarose and agar, casting the mixture into a mold, cooling of the mixture obtained for thermal gelling and molding, removal from the mold and then gelling by chemical crosslinking, by bringing into contact with a calcium saline solution.

8. A molded gel implant consisting essentially of a biocompatible and gellable aqueous composition of polysaccharides consisting of a mixture of two polysaccharides, wherein one of the two polysaccharides is chemically gellable and the other of the two polysaccharides is thermally gellable, wherein the molded gel implant is prepared by:

preparing a composite gel that comprises the biocompatible and gellable aqueous composition of polysaccharides, by:

solubilization of the chemically gellable polysaccharide in water, wherein the chemically gellable polysaccharide is an alginate, addition of the thermally gellable polysaccharide and dissolving by heating, wherein the thermally gellable polysaccharide is selected from the group consisting of agarose and agar, homogenization of the mixture, casting the mixture into a mold, cooling of the mixture obtained for thermal gelling and molding, and removing the thermally gelled and molded composition from the mold and then gelling by chemical crosslinking by bringing the thermally gelled and molded composition into contact with a calcium saline solution to obtain the molded gel implant.

9. A molded gel implant consisting essentially of a biocompatible and gellable aqueous composition of polysaccharides, the composition consisting of a mixture of two polysaccharides, wherein one of the two polysaccharides is chemically gellable and the other of the two polysaccharides is thermally gellable, wherein the chemically gellable polysaccharide is an alginate, wherein the thermally gellable polysaccharide is selected from the group consisting of agarose and agar, and wherein the molded gel implant is obtained by thermal gelling followed by chemical gelling of the biocompatible and gellable aqueous compositions by bringing the biocompatible and gellable aqueous compositions into contact with a calcium saline solution.

10. The molded gel implant as claimed in claim 1, wherein the chemically gellable polysaccharide is a calcium alginate and the thermally gellable polysaccharide is an agarose.

11. The molded gel implant as claimed in claim 2, wherein the chemically gellable polysaccharide is a calcium alginate and the thermally gellable polysaccharide is agarose.

12. The molded gel implant as claimed in claim 3, wherein the chemically gellable polysaccharide is a calcium alginate and the thermally gellable polysaccharide is agarose.

\* \* \* \* \*